(12) United States Patent
Han

(10) Patent No.: US 8,921,037 B2
(45) Date of Patent: Dec. 30, 2014

(54) PF4-DEPLETED PLATELET RICH PLASMA PREPARATIONS AND METHODS FOR HARD AND SOFT TISSUE REPAIR

(75) Inventor: Bo Han, Los Angeles, CA (US)

(73) Assignee: Bo Han, Temple City, CA (US)

(*) Notice: Subject to any disclaimer, the term of this patent is extended or adjusted under 35 U.S.C. 154(b) by 346 days.

(21) Appl. No.: 12/639,918

(22) Filed: Dec. 16, 2009

(65) Prior Publication Data
US 2010/0150892 A1 Jun. 17, 2010

Related U.S. Application Data

(60) Provisional application No. 61/138,057, filed on Dec. 16, 2008.

(51) Int. Cl.
*A01N 1/02* (2006.01)
*A61K 35/14* (2006.01)
*A61K 35/16* (2006.01)

(52) U.S. Cl.
CPC .......... *A61K 35/14* (2013.01); *A61K 35/16* (2013.01); *A61K 35/19* (2013.01)
USPC .............................. 435/2; 514/13.8

(58) Field of Classification Search
None
See application file for complete search history.

(56) References Cited

U.S. PATENT DOCUMENTS

| | | | |
|---|---|---|---|
| 5,304,542 A * | 4/1994 | Tatakis | 514/16.9 |
| 2005/0100536 A1* | 5/2005 | Mishra | 424/93.72 |
| 2006/0085003 A1* | 4/2006 | Schmieding et al. | 606/73 |
| 2007/0141036 A1* | 6/2007 | Gorrochategui Barrueta et al. | 424/93.7 |

OTHER PUBLICATIONS

Rucinski et al., Blood vol. 53, No. 1, 1979.*
Horton et al., Biochimica et Biophysica Acta, 630 (1980) 459-462.*
Barrow, C. R. and Pomeroy, G.C., "Enhancement of syndesmotic fusion rates in total ankle arthroplasty with the use of autologous platelet concentrate," Foot Ankle Int 26(6): 458-461, 2005.
Berghoff, W. J. et al., "Platelet-rich plasma application during closure following total knee arthroplasty," Orthopedics 29(7): 590-598, 2006.
Bibbo, C. et al., "Union rates using autologous platelet concentrate alone and with bone graft in high-risk foot and ankle surgery patients," J Surg Orthop Adv, 14(1): 17-22, 2005.
Everts, P. A. et al., "Platelet-rich plasma preparation using three devices: implications for platelet activation and platelet growth factor release," Growth Factors, 24(3): 165-171, 2006.
Everts, P. A. et al., "Platelet-rich plasma and platelet gel: a review," J Extra Corpor Technol, 38(2): 174-187, 2006.
Frechette, J. P. et al., "Platelet-rich plasmas: growth factor content and roles in wound healing," J Dent Res, 84(5): 434-439, 2005.
Froum, S. J. et al., "Effect of platelet-rich plasma on bone growth and osseointegration in human maxillary sinus grafts: three bilateral case reports," Int J Periodontics Restorative Dent, 22(1): 45-53, 2002.
Maione, T. E. et al., "Inhibition of angiogenesis by recombinant human platelet factor-4 and related peptides," Science, 247(4938):77-79, 1990.
Nikolidakis, D. J. et al., "The effect of platelet-rich plasma on the bone healing around calcium phosphate-coated and noncoated oral implants in trabecular bone," Tissue Eng, 12(9): 2555-2563, 2006.
Ranly, D. M. et al., "Platelet-rich plasma inhibits demineralized bone matrix-induced bone formation in nude mice," J Bone Joint Surg Am, 89(1): 139-147, 2007.
Scheuerer, B. et al., "The CXC-chemokine platelet factor 4 promotes monocyte survival and induces monocyte differentiation into macrophages," Blood, 95(4): 1158-1166, 2000.
Van Den Dolder, J. et al., "Platelet-rich plasma: quantification of growth factor levels and the effect on growth and differentiation of rat bone marrow cells," Tissue Eng, 12(11): 3067-3073, 2006.
Weiner, B. K. and Walker, M., "Efficacy of autologous growth factors in lumbar intertransverse fusions," Spine, 28(17): 1968-1970, 2003.
Wolpe, S. D. and Cerami, A., "Macrophage inflammatory proteins 1 and 2: members of a novel superfamily of cytokines," FASEB J, 3(14): 2565-2573, 1989.
Xia, C. Q. and Kao, K.J., "Effect of CXC chemokine platelet factor 4 on differentiation and function of monocyte-derived dendritic cells," Int Immunol, 15(8): 1007-1015, 2003.
Zechner, W. S. et al., "Influence of platelet-rich plasma on osseous healing of dental implants: a histologic and histomorphometric study in minipigs," Int J Oral Maxillofac Implants, 18(1): 15-22, 2003.

* cited by examiner

*Primary Examiner* — Allison Fox
*Assistant Examiner* — Yvonne Pyla
(74) *Attorney, Agent, or Firm* — Greenberg Traurig, LLP

(57) ABSTRACT

Methods of repairing and regenerating hard or soft tissue and reducing inflammation, anti-angiogenesis and anti-osteogenesis in a mammal and related methods of removing PF4 from platelets containing blood preparations. In one embodiment, the method comprises administering to a mammal platelets containing blood preparation where the PF4 has been reduced from the platelet containing blood preparation to repair and regenerate hard and soft tissue in the mammal.

24 Claims, 5 Drawing Sheets

PF4-DEPLETED PLATELET RICH PLASMA PREPARATIONS AND METHODS FOR HARD AND SOFT TISSUE REPAIR

RELATED APPLICATION

This application claims the benefit of and priority to U.S. Provisional Application Ser. No. 61/138,057, filed Dec. 16, 2008, the contents of which are incorporated by reference herein in its entirety.

BACKGROUND

1. Field

The present disclosure relates generally providing platelet containing blood preparation, including platelet-rich-plasma (PRP) that provides numerous benefits and advantages. More specifically, the present disclosure relates to providing platelet-rich plasma with little to no platelet factor 4 (PF4), a most abundant pre-inflammatory protein in PRP which, among other things, reduces inflammation, anti-angiogenesis and anti-osteogenesis and plays a role in soft and hard tissue repair and regeneration in a mammal. Additionally, the present disclosure relates to a method of removing PF4 from platelets containing blood preparations.

2. General Background

Platelet rich plasma (PRP) concentrated from blood, has attracted the attention of researchers as a good source of growth factors. When it is processed from the patient's autologous blood, potential hazard to the patient is low. It is also cost-effective. The use of platelet-rich plasmas (PRPs) has increased significantly over the last decade in the fields of orthopedics, periodontics, maxillofacial surgery, urology, and plastic surgery. The healing potential of PRP is often attributed to the release of multiple growth factors from the highly concentrated platelets. Growth factors released from platelets are believed to include, among other things, platelet-derived growth factor (PDGF), TGF-β, platelet-derived epidermal growth factor (PDEGF), platelet-derived angiogenesis factor (PDAF), and insulin-like growth factors I (IGF-I) and VEGF. These peptide factors alone or in concert with others have mitogenic and chemotactic effects on cells for tissue repair and regeneration.

When PRP is used adjuvant for tissue repair and regeneration, much attention has been paid to the growth factors, such as PDGF, TGF-β and IGF in PRP. Their mitogenic and chemotaxic effect to the mesenchymal stem cell and progenitor cells have been studied extensively in vitro and in vivo. However, when platelets are activated, large amounts of cytokines and chemokines are also released simultaneously with growth factors. Platelets and many of their products are now recognized as playing important roles in the immunoregulation and differentiation of various cell types. During acute vascular injury or chronic disease, activated platelets release a variety of mediators, including three members of the chemokine family, the connective tissue-activating peptide III, RANTES, and the platelet factor 4 (PF4[1]). Among them, the most abundant protein is PF4.

Platelet factor 4 (PF4) is a major secretory protein of activated platelets with molecular weight of 70 kD (1). As a member of the CXC chemokines, PF4 participates in inflammatory responses by attracting monocytes and neutrophils (Xia and Kao 2003). PF4 promotes monocyte survival and induces the differentiation of monocytes into macrophages and is involved in long-term regulatory processes of these cells and might support the differentiation of infiltrating monocytes into macrophages in vivo during intermediate and late stages of an inflammatory process (Scheuerer, Ernst et al. 2000). PF4 possesses characteristic structural features of the pro-inflammatory proteins interleukin-8 and beta-thromboglobulin and has been shown to be chemotactic for neutrophils and monocytes in vivo (Wolpe and Cerami 1989). This similarity of the structure and activities of PF4 to well characterized pro-inflammatory proteins along with the ubiquitous aggregation of platelets at sites of inflammation suggest that PF4 may be an endogenous mediator of inflammation. Thus, it is anticipated that swelling could accompany the administration of PF4 in vivo.

PF4 has been shown to have antiangiogenic properties both in vitro and in vivo (Maione, Gray et al. 1990). Recombinant human PF-4 inhibits blood vessel proliferation in the chicken chorioallantoic membrane assay in a dose-dependent manner. PF-4 inhibits angiogenesis by associating directly with FGF-2, inhibiting its dimerization and blocking FGF-2 binding to endothelial cells. Recombinant human PF-4 has been tested in clinical trials that include Kaposi's sarcoma, colon and kidney carcinomas, and melanoma. In particular, intralesional injection of PF-4 is effective in the treatment of Kaposi's sarcoma.

PF4 also inhibits osteoblast proliferation. It may be used to treat diseases associated with localized changes in bone metabolism in which abnormal osteoblastic cell function/activity contributes to pathogenic bone changes (See U.S. Pat. No. 5,304,542 to Tatakis, entitled "Use Of Platelet Factor 4 To Inhibit Osteoblast Proliferation").

SUMMARY OF THE INVENTION

In one embodiment of the present disclosure, a method is provided for repairing and regenerating hard or soft tissue in a mammal. The method comprises administering to a mammal platelets containing blood preparation where the naturally-occurring PF4 level has been reduced from the platelets containing blood preparation to repair and regenerate hard and soft tissue in the mammal.

In another embodiment of the present disclosure, PF4 depleted platelets containing blood preparation that is platelet-rich plasma, is used alone or with other bone grafts for bone defect repair.

In yet another aspect of at least one embodiment of the present disclosure, the bone grafts include but are not limited to collagen sponge, collagen sheet, hydroxapatite granule, hydroxyapatite block, freeze-dried bone allograft (FDBA) demineralized bone matrix, TCP, bioglass, or other osteoconductive bone grafts.

In yet another embodiment of the present disclosure, PF4 depleted platelets containing blood preparation are mixed with cells from the mammal before being administered to a mammal.

In yet another aspect of at least one embodiment, the cells from the mammal are from the mammal's blood, cells from the mammal's bone marrow, fat tissue, muscle tissue or allogenic stem cells.

In yet another aspect of at least one embodiment of the present disclosure, the PRP-depleted PF4 composites are applied to diseased or degenerated sites, including but not limited to, joints, meniscus, tendon, ligament, skin, chronic wound, peripheral nerve, or other operation sites.

In yet another embodiment of the present disclosure, a method is provided for removing PF4 from platelets containing blood preparation. The method comprises (a) providing platelets containing blood preparation, (b) activating the platelets of the platelet-containing blood preparation by adding to the platelets containing blood-preparation a platelet-activation reagent, (c) adding heparin that is conjugated to a solid or semi-solid phase matrix to the platelets containing blood-preparation and (d) removing the heparin that is conjugated to a solid or semi-solid phase matrix from the platelet containing blood preparation.

In yet another embodiment of the present disclosure, a method is provided for removing PF4 from platelets containing blood preparation. The method comprises (a) providing platelets containing blood preparation, (b) activating the platelets of the platelet-containing blood preparation by adding a platelet-activation reagent to the platelet-containing blood preparation or by storing the platelets long enough to cause spontaneous activation, (c) passing the platelet-containing blood preparation through a heparin affinity column to remove at least some of the PF4 from the platelet-containing blood preparation.

In yet another aspect of the present disclosure, heparin that is conjugated to a solid or semi-solid phase matrix binds to at least some of the PF4 of the platelet-containing blood preparation.

In yet another aspect of at least one embodiment of the present disclosure, the platelet-activation reagent is one or more items selected from the group of calcium, thrombin, collagen, Wf, thromboxane A2 or ADP.

In yet another aspect of the present disclosure, the heparin-conjugated solid or semi-solid matrix is removed by filtration, centrifugation, sedimentation or other known methods.

In yet another aspect of at least one embodiment of present disclosure, the platelet-containing blood preparation flows through a solid or semi-solid heparin-conjugated matrix by a mechanical force selected from gravity, pressure, osmosis.

In yet another aspect of at least one embodiment of the present disclosure, the solid or semi-solid phase heparin-conjugated matrix is one or more items selected from the group of beads, mesh, column, hollow fibers or gel. One example of a heparin-conjugated matrix is heparin-conjugated agarose beads purchased from Thermo Fisher Scientific Inc. (Waltham, Mass.).

In yet another aspect of at least one embodiment of the present disclosure, the binding of the heparin to a solid phase heparin-binding matrix to at least some of the PF4 of the platelet-containing blood preparation occurs by one or more methods selected from the group of mass loading, batch loading, sequential loading and continuous loading.

In yet another aspect of at least one embodiment of the present disclosure, the platelet-containing blood preparation is whole blood.

In yet another aspect of at least one embodiment of the present disclosure, the platelet-containing blood preparation is platelet-rich plasma.

In yet another aspect of at least one embodiment of the present disclosure, the solid phase heparin-binding matrix is heparin-conjugated agarose.

In yet another aspect of at least one embodiment of the present disclosure, the platelet-activator reagent is one or more items selected from the group of thrombin, collagen, thromboxane A2 and ADP. It should be appreciated that it is within the scope of the present disclosure to use any known platelet activator reagent.

In yet another embodiment of the present disclosure, a method is provided for reducing inflammation, anti-angiogenesis and anti-osteogenesis in the soft and hard tissue of a mammal. The method comprises administering to a mammal platelets containing blood preparation where the naturally occurring PF4 level has been reduced from the platelet-containing blood preparation in order to reduce inflammation, anti-angiogenesis and anti-osteogenesis in the mammal.

In yet another aspect of at least one embodiment of the present disclosure, the platelet-containing blood preparation is whole blood.

In yet another aspect of at least one embodiment of the present disclosure, the platelet-containing blood preparation is platelet-rich plasma.

In yet another aspect of at least one embodiment of the present disclosure, the PF4 reduced platelet-containing blood preparation is administered to the mammal with a bone graft.

In yet another aspect of at least one embodiment of the present disclosure, the platelet-rich plasma is obtained from an autologous blood donor.

In yet another aspect of at least one embodiment of the present disclosure, the solid or semi-solid phase heparin-conjugating matrix is one or more items selected from the group of: heparin-conjugated agrose beads, heparin-conjugated silica beads, heparin-conjugated Sepharose beads, heparin-Sephadex beads, heparin-conjugated alginate beads, heparin-conjugated acrylic beads, or other polymer, polypeptide, polysaccharide used for conjugating heparin. The solid or semi-solid matrix is in forms of packed beads, column, 3D mesh, hollow fibers and gel.

In yet another aspect of at least one embodiment of the present disclosure, the solid or semi-solid phase heparin-conjugating matrix is one or more items selected from the group of: heparin-conjugated agrose beads, heparin-conjugated silica beads, heparin-conjugated Sepharose beads, heparin-Sephadex beads, heparin-conjugated alginate beads, heparin-conjugated acrylic beads, or other polymer, polypeptide, polysaccharide used for conjugating heparin and In yet another aspect of at least one embodiment of the present disclosure, the solid or semi-solid phase heparin-conjugating matrix is in the form of packed beads, column, 3D mesh, hollow fibers and/or gel.

In yet another aspect of at least one embodiment of the present disclosure, the platelet-containing blood preparation is administered to a wound site of the mammal.

In yet another aspect of at least one embodiment of the present disclosure, the platelet-containing blood preparation is administered with one or more items selected from the group of bone graft, wound dressing, skin graft, cartilage graft, ligament or tendon grafts and peripheral nerve graft.

In yet another aspect of at least one embodiment of the present disclosure, the platelet-containing blood preparation is combined with one or more cells selected from the group of: tissue-specific cells, stem cells, autologous cells and allogenous cells, before it is administered to the mammal.

In yet another embodiment of the present disclosure, a method of further processing a platelets containing blood preparation for repairing and regenerating hard or soft tissue in a mammal and treating wounds is provided. The method comprises, binding and removing 40% to 100% of the naturally-occurring PF4 from the platelets containing blood preparation and administering the PF4-reduced platelets containing blood preparation to the mammal.

FIGURE DESCRIPTIONS

The above-mentioned features and objects of the present disclosure will become more apparent with reference to the following description taken in conjunction with the accompanying drawings wherein like reference numerals denote like elements and in which:

FIG. 1 shows a bar graph depicting the results of experiments where PF4 was tested in the PRP preparation with PF4

ELISA test kit (Duoset Human PF4, R&D). PF4 can be released from platelets by endogenous thrombin activation (48 hours, room-temperature storage) or by exogenous thrombin (100 units bovine thrombin) and calcium chloride activation.

FIG. 2 shows a bar graph depicting the results of experiments where PF4 binds to heparin and can be removed from PRP. Soluble heparin and agarose-conjugated heparin beads (Sigma) were added into thrombin-activated PRP. PF4 concentration was determined by PF4 ELISA methods.

FIG. 3 shows a bar graph depicting the results of experiments where TGF-β activity in PRP was intact before and after PF4 removal by heparin. TGF-β activity was tested by transformed mink lung cells (TMCL) with PAI-1 promoter/luciferase reporter.

FIG. 4 shows two bar graphs depicting the results of experiments where PF4 was released from platelets by spontaneous activation. Whole blood was stored at room temperature up for different periods of time (A: 30 min), B: 24 hours, C: 48 hours). At different times, whole blood was separated by centrifugation to separate PPP and PRP from other blood cells. The effects of PPP and PRP were tested on SaoS-2 cell proliferation by MTT method.

Figure 6:
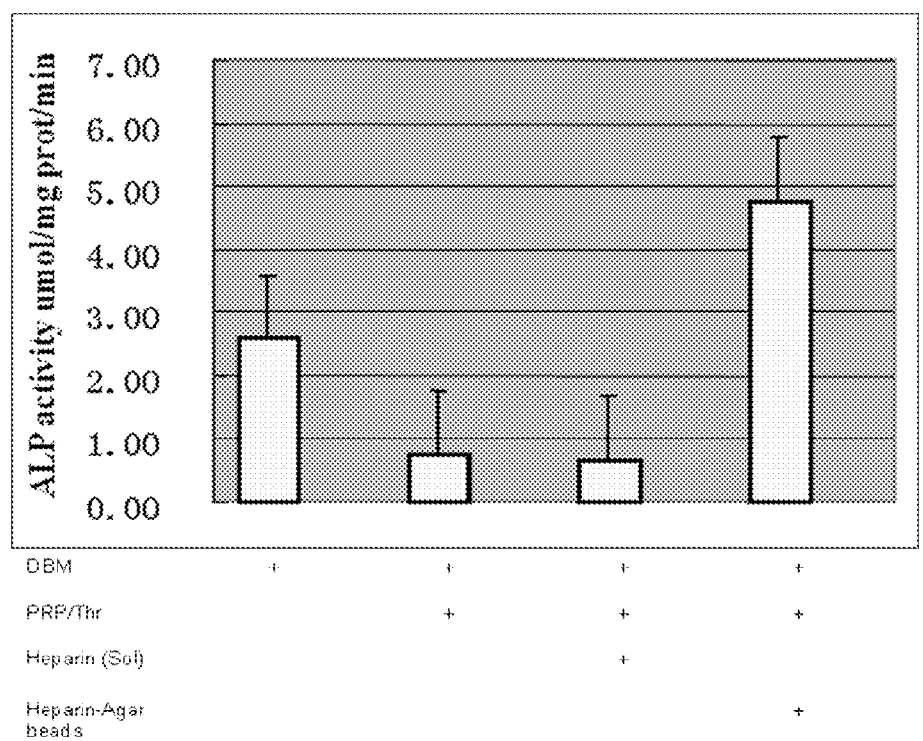

FIG. 6 shows a bar graph depicting the results from experiments regarding alkaline phosphatase activity in demineralized bone matrix (DBM) explants. Human DBM in nude rats were implanted with following groups for 28 days. (1) DBM alone, (2) DBM plus thrombin-activated PRP, (3) DBM plus thrombin-activated PRP with the addition of a heparin solution, (4) DBM plus thrombin-activated PRP with heparin-agarose beads.

Figure 7:
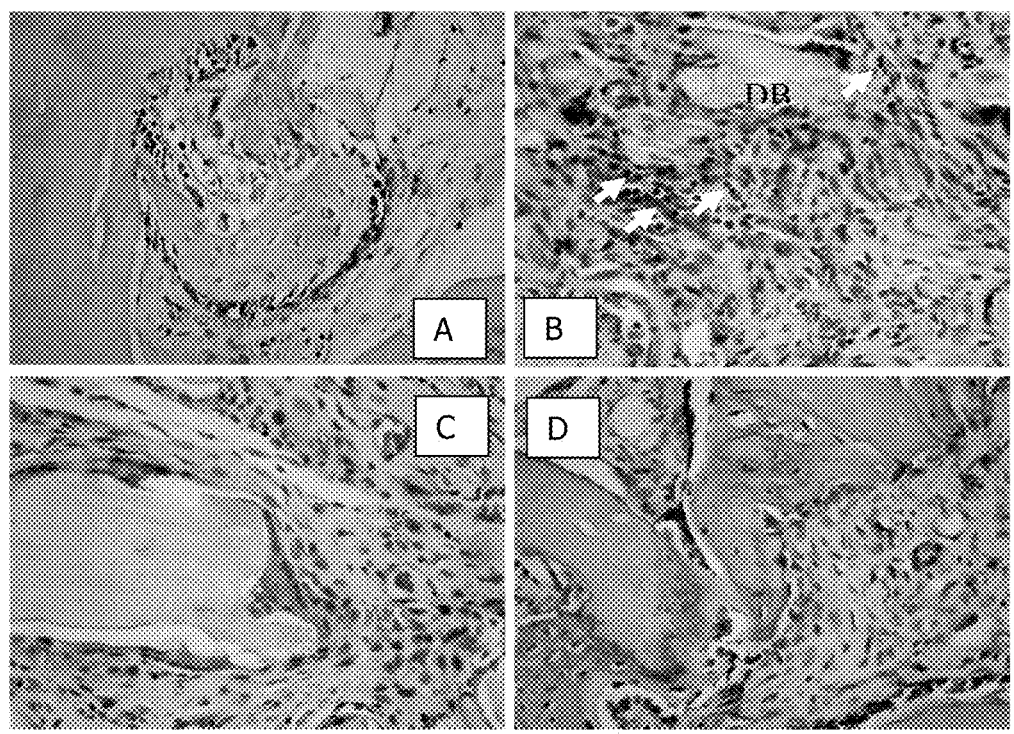

FIG. 7 depicts histological micrographs of DBM implanted for 4 weeks in nude rat ectopic intramuscular models. (A) DBM alone, (B) DBM plus thrombin-activated PRP, (C) DBM plus thrombin-activated PRP with the addition of a heparin solution, (D) DBM plus thrombin-activated PRP with heparin-agarose beads.

DETAILED DESCRIPTION

PRP is used adjuvant for tissue repair and regeneration. PRP is typically prepared and used in a gel form by adding a clinical dose of bovine thrombin or concentrated autologous thrombin and calcium to induce fibrin clot formation (Froum, Wallace et al. 2002). Thrombin not only catalyzes the conversion of fibrinogen into fibrin to give the PRP clot mechanical and improved handling properties (Berghoff, Pietrzak et al. 2006), but also triggers platelet aggregation and degranulation (Everts, Brown Mahoney et al. 2006; Everts, Knape et al. 2006). Thrombin causes the platelets to simultaneously release their growth factors and chemikines including PF4. PF4 is also released during aggregation by ADP, epinephrine, and collagen.

Figure 1:
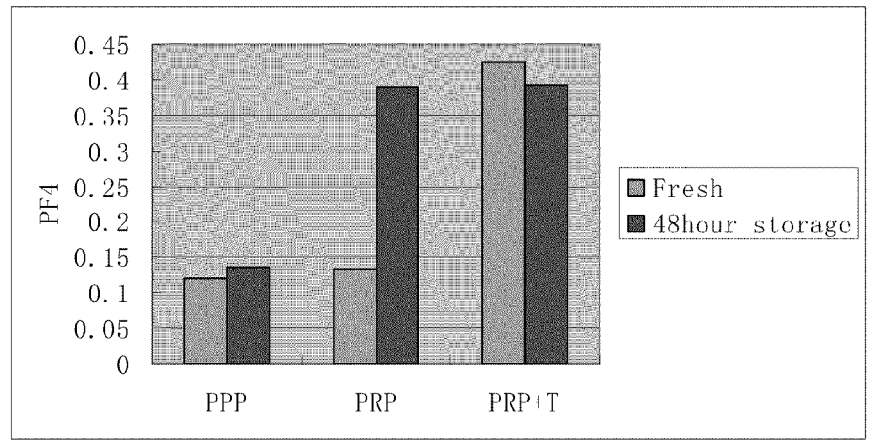

FIG. 1 shows the results of experiments where PF4 was tested in the PRP preparation with PF4 ELISA test kit (Duoset Human PF4, R&D). PF4 can be released from platelets by endogenous thrombin activation (48 hours, room temperature storage) or by exogenous thrombin (100 units bovine thrombin) activation.

Since PF4 is a heparin-binding protein, heparin can be used to remove PF4 from PRP preparation. The results of the experiments shown in FIG. 2 demonstrate that PF4 concentration decreased significantly when either soluble heparin or solid phase heparin were added into thrombin-activated PRP preparation.

Figure 2:
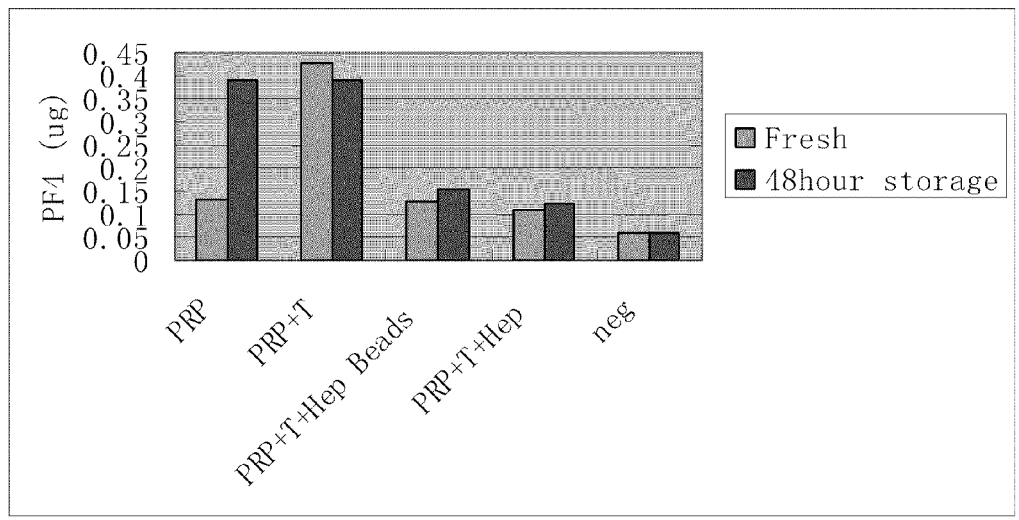

As demonstrated by the experimental results shown in FIG. 2. PF4 binds to heparin and can be removed from PRP. Soluble heparin and agarose-conjugated heparin beads (Sigma) were added into thrombin-activated PRP. PF4 concentration was determined by PF4 ELISA methods.

The results of the experiments shown herein also demonstrate that the process of removal of PF4 in PRP does not interfere with other growth factors' content and activity. TGF-β was selected as a representative growth factor in PRP and its activity was tested before and after heparin treatment. The results of the experiments shown in FIG. 3 demonstrate that TGF-β activity was not decreased when heparin was used to deplete PF4.

Figure 3:
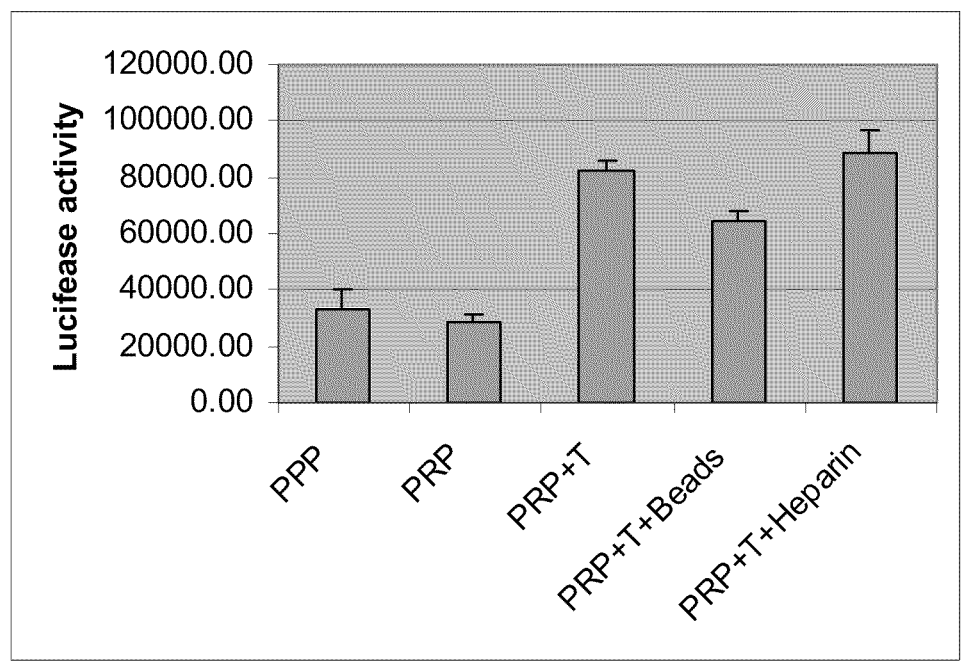

The results of experiments shown in FIG. 3 also demonstrate that TGF-β activity in PRP was intact before and after PF4 removal by heparin. TGF-β activity was tested by transformed mink lung cells (TMCL) with PAI-1 promoter/luciferase reporter.

Figure 4:
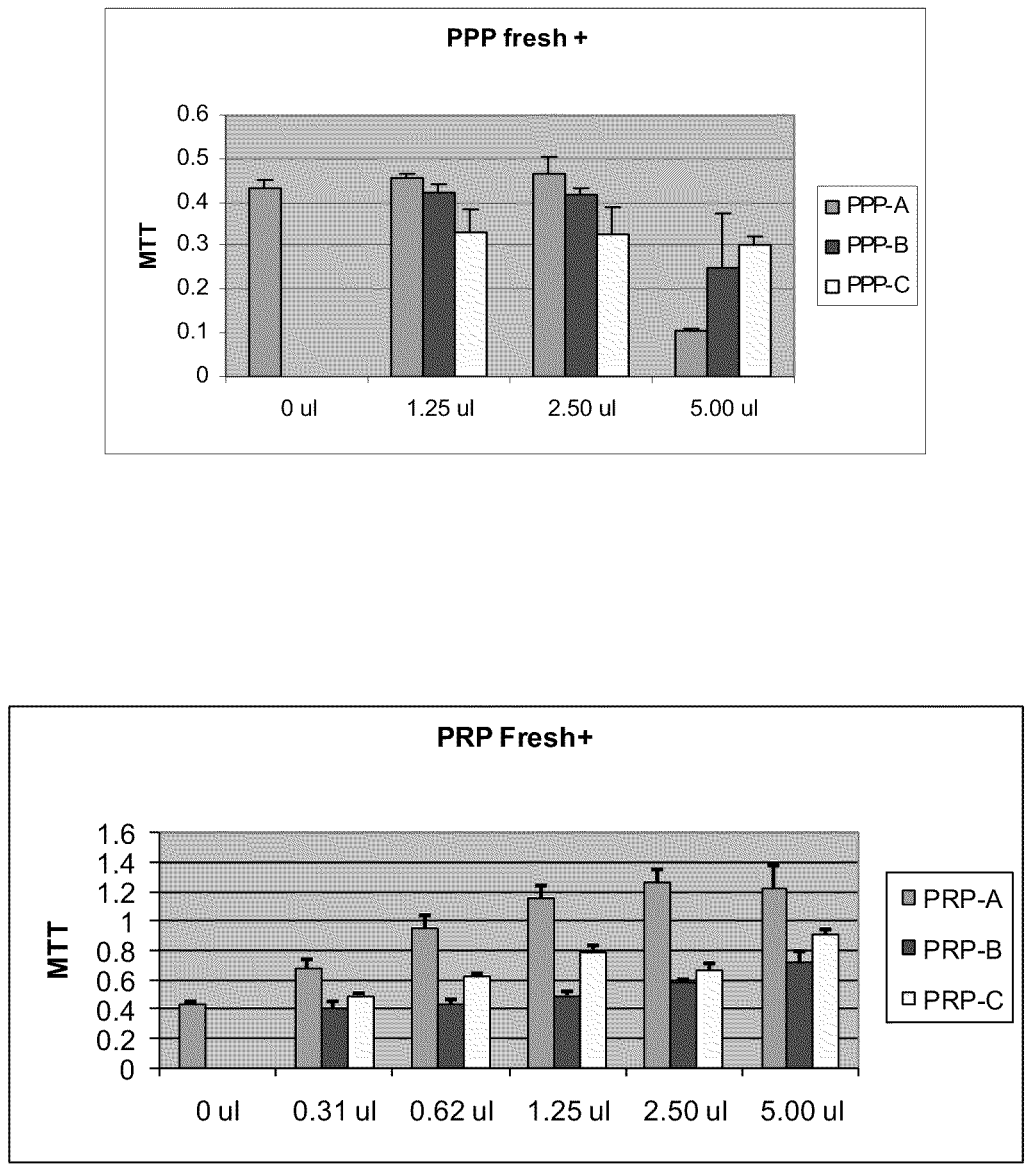

The results of the experiments shown in FIG. 4 demonstrate that PF4 released from platelets by spontaneous activation. Whole blood was stored at room temperature up for different periods of time (A: less than 1 hour), B: 24 hours, C: 48 hours). At different times, whole blood was separated by centrifugation to separate PPP and PRP from other blood cells. The effects of PPP and PRP were tested on SaoS-2 cell proliferation by MTT method. FIG. 4 indicates that the overall net mitogenic effects (represented by cell viability) are dependent on the release of growth factors, cytokines and chemokines from blood cells. Storage conditions have significant effects on the release of biological active molecules.

Figure 5A:
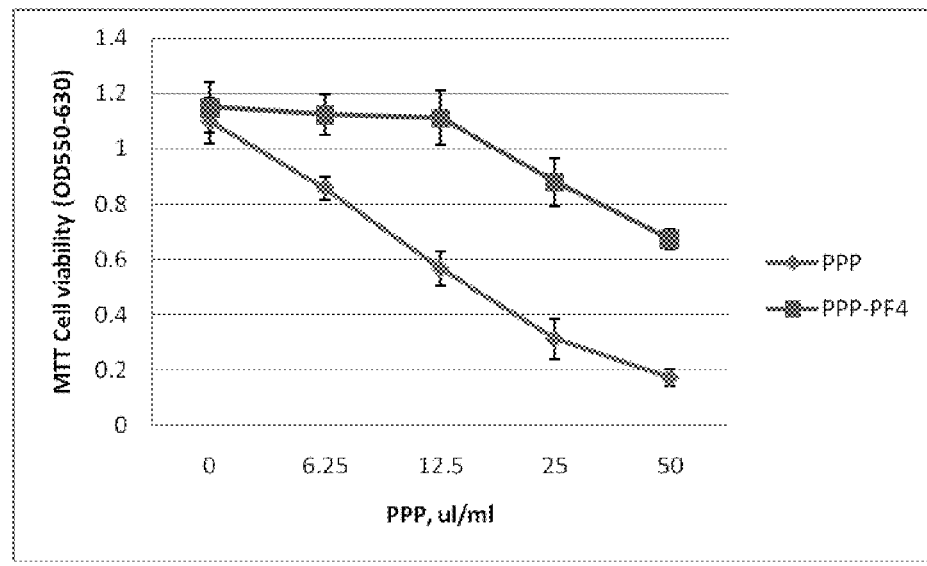
FIG. 5A shows a line graph depicting the results from experiments where SaoS-2 cell proliferation was inhibited activated PPP in a dose-dependent manner. After treating with heparin-agarose beads, PPP's inhibition effect was relieved significantly.
Figure 5B:
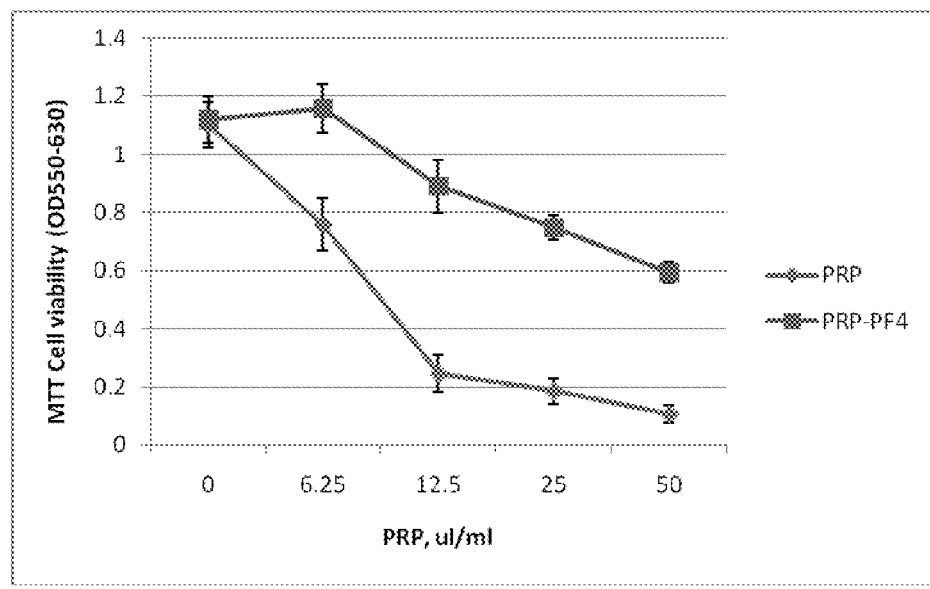
FIG. 5B shows a line graph depicting the results from experiments where SaoS-2 cell proliferation was inhibited PRP in a dose-dependent manner. After treating with heparin-agarose beads, PRP's inhibition effect was relieved significantly.

Inhibition of osteosarcoma cell proliferation by blood preparation can be rescued by removing PF4. Thirty cubic centimeters (cc) of blood were drawn from a healthy male donor. Blood components were separated into PPP, PRP and RBC by centrifugation. Aliquots of PPP and PRP were activated by thrombin as previously described. In 1 cc of blood preparation, 100 ul of heparin-agarose beads (Sigma) were added. After 5 minutes of gentle mixing, supernatant was collected after spinning down the beads. Different volumes of blood preparation were added to the cell culture of SaoS-2 cells (96 well plate, 6×10^4 cell/well) in 1% FBS/DMEM. Cell viability was determined by MTT assay. SaoS-2 cell proliferation was inhibited activated PPP in a dose-dependent manner. After treatment with heparin-agarose beads, PPP's inhibition effect was relieved significantly. FIG. 5A shows that SaoS-2 cell proliferation was inhibited PRP in a dose dependent manner. After treated with heparin-agarose beads, PRP's inhibition effect was relieved significantly, as shown in FIG. 5B.

PRP has been proposed as an autologous source of growth factors that can be used clinically as an adjuvant to enhance the quantity, quality, and rate of bone regeneration induced by DBM (Frechette, Martineau et al. 2005; van den Dolder, Mooren et al. 2006). However, controversies persist in the literature regarding its benefits for bone regeneration. Ranly et al. demonstrated that PRP, when activated by thrombin, could decrease the osteoinductivity of DBM in athymic mouse model (Ranly, Lohmann et al. 2007). Other publications have implicated thrombin-activation of PRP with diminished bone stimulation. In a goat study, PRP significantly increased the bone contact around a calcium phosphate-coated implant compared to controls, while PRP activated with thrombin (300 U/ml in 10% $CaCl_2$) did not (Nikolidakis, van den Dolder et al. 2006). In a mini-pig model, thrombin-activated PRP (0.5 ml Tissucol thrombin-fibrin solution) failed to show any statistically significant effects on peri-implant bone formation after a 6-week healing period (Zechner, Tangl et al. 2003). Even though clinically improved bone fusion has been achieved with the augmentation of graft material with PRP (Barrow and Pomeroy 2005; Bibbo, Bono et al. 2005), adverse effects on bone graft consolidation have been reported (Weiner and Walker 2003).

Human DBM in nude rats were implanted with following groups for 28 days. (1) DBM alone, (2) DBM plus thrombin-activated PRP, (3) DBM plus thrombin-activated PRP with addition of heparin solution, (4) DBM plus thrombin-activated PRP with heparin-agarose beads. The results of experiments shown in FIG. 6 demonstrate that DBM with thrombin-activated PRP had lower ALP activity than DBM alone. The addition of a heparin solution to DBM/PRP also decreased ALP. However, when solid phase heparin beads were added to sequester PF4 in PRP solution, ALP activity significantly increased. ALP activity is a biochemical marker that correlates well with bone formation potential in this animal model.

Histological results confirmed this finding (FIG. 7). In the athymic rat intramuscular implantation, most cartilage is replaced by osteoblasts, osteocytes, and bone marrow in 28 days. DBM bone formation is determined histologically. DBM alone exhibits osteoinductivity with islands of bone marrow and new bone forming in-between the residual DBM particles (FIG. 7A). However, thrombin-activated PRP dramatically decreased the bone formation potential of the DBM. No bone marrow or new bone is seen, and the residual DBM particles are surrounded by fibrous tissue. Subchronic inflammation, which is rated as medium to severe, is persistent in the thrombin-activated groups (FIG. 7B). In the PRP treated with heparin-agarose group, much more bone marrow and new bone is evident (FIG. 7D). The bone score is higher than the group receiving DBM alone. However, if PRP is added in solution form, inhibitory instead of stimulatory effects are evident on DBM bone formation (FIG. 7C).

A DBM heterotopic bone formation model was used to assess the supplementary effects of PRP on DBM osteoinductivity. Since it is immune compromised rat model, human DBM and human PRP can be tested. The effects of PRP as an adjuvant for bone grafts to enhance the quantity and quality of bone regeneration is based on the premise that PRP preparations provide an autologous natural combination of rapidly available growth factors to the wound sites. However, when PRP was activated by adding thrombin and calcium, the cellular effects of combined growth factors and chemokines with elevated concentration from PRP activation were eliminated. Inhibitory effects were observed on new bone cell formation. It is possible that negative factors such as PF4 have been released by thrombin activation, which neutralized the positive effect of other mitogenic factors. It is correlated with in vitro assay that PF4 inhibits osteoblast proliferation. When PF4 was depleted by heparin-agarose, the inhibition effect was relieved. In animal models, when activating PRP without removing PF4, significantly more inflammatory cells were found between DBM particles in the thrombin-activated PRP group, including macrophages and monocytes. This data confirmed that PF4 is a pro-inflammatory factor with chemotactic effect on monocyte and marcophages.

If a heparin solution was added to the PRP to sequester PF4 effect, no effect or inhibitory effect was noticed. This result confirms that soluble heparin is not effective to diminish PF4 effect.

When PRP was treated with heparin-conjugated agarose beads (Sigma), the PF4 content decreased three times compared with the untreated one. Bone formation effect of DBM was increased by approximately 100%. PRP is a possible adjuvant for wound repair because of the mitogenic, chemoattractant, and angiogenic growth factor profile in PRP. PF4 was proved an anti-angiogenic factor and anti-osteogenic factor. This result proves that one-step treatment of PRP to remove PF4 has changed the composition of PRP and the changed formulation is effective for wound repair.

Methods

PRP Preparation

For one lot of PRP preparation, 27 milliliters (ml) of blood were collected into 30 ml syringes pre-filled with 3 ml of anticoagulant citrate dextrose A (ACD-A) from healthy donors (28-42 years old). PRP was prepared with the GPS® II system (Biomet Biologics, Warsaw, Ind.). After centrifugation at 3200 rpm for 15 minutes, three basic components, red blood cells, PRP, and platelet-poor plasma (PPP), were separated.

Another way to prepare PRP was to centrifuge blood at 194×g for 10 minutes at room temperature to obtain PRP and twice at 2500×g for 10 minutes at room temperature to obtain PPP. Platelets were counted using visible light microscope.

Thrombin Activation of PRP with or without Calcium

In the vial with 2 mls of PRP, 200 μl of thrombin either activated with Thrombin/Ca (Jones Pharma Inc., Bristol, Tenn., bovine origin, 300 U/ml in 10% $CaCl_2$) or thrombin without Ca (Sigma, St. Louis, Mo., USA, reconstituted with saline, 300 U/ml) was added followed by vortexing. After incubating 10 minutes at room temperature, clotted PRP was centrifuged at 12 k rpm (Eppendorf) for 10 minutes. Resulting supernatants were removed to a new vial and used for in vitro studies and in vivo studies.

Whole blood, PRP and PPP were also activated with endogenous thrombin. Blood preparation was also stored at room temperature for up to 72 hours.

PRP Growth Factor Profile and PF4 Content

The levels of TGF-β1 (Human TGF-β1 Quantikine ELISA Kit, DB100B), VEGF (Human VEGF Quantikine ELISA Kit, DVE00) and PDGF-BB (Human PDGF-BB Quantikine ELISA Kit, DBB00) in the PRP, PPP, and whole blood were measured by using a commercially available enzyme-linked immunosorbent assay (ELISA) kit (all kits, R&D Systems, Minneapolis, Minn.). PF4 was tested by Duoset Human PF4 (R&D).

PRP and whole blood samples were tested by optical densities of the microplate wells with a microplate reader (Molecular Devices, Sunnyvale, Calif.) at 405 nm.

TGF-β was selected as a representative growth factor in PRP and its activity was tested before and after thrombin activation. TGF-β exists in both a latent and active form. The latent form has a c-terminal pro-region that must be cleaved in order for the protein to interact with a TGF-β receptor. TGF-β activity in the PRP with and without thrombin activation was assayed by mink lung cells transfected with plasminogen activator inhibitor-1 (PAI-1) promoter-luciferase reporter. Briefly, PAI-1-Luc transformed mink lung cells were plated in a 48-well culture plate at a density of 90,000 cells/well in 10% fetal bovine serum (FBS, Hyclone, Logan, Utah)/ DMEM (Mediatech, Herndon, Va.) containing 200 μg/ml geneticin (G418 Clontech Laboratories, Inc., Mountain View, Calif.) and allowed to attach for 5.0 hours at 37 degrees C.

After washing twice with DMEM, aliquots of PRP were added in a 0.5% FBS/DMEM test medium. After 17 hours, cells were rinsed twice with ice-cold PBS before testing for luciferase activity using a luciferase assay kit (Promega, Madison, Wis.). Only active TGF-β in PRP contributes to the PAI-1 linked Luciferase activity.

Depletion of PF4

In each 1 ml of blood preparations, 100 ul of heparin or heparin-agarose beads suspension (Sigma, H0402) were added. Vortex vigorously and centrifugation at 10 k for 1 minute. Supernatant which is depleted of PF4 was collected by a transfer ring to a new Eppendorf tube. Beads in the precipitation were discarded.

Animal Studies

Bone formation: athymic rats (150-175 g, Harlan Inc., IN) were used in the study. Six muscle pouches were created in the abdominal muscles, six on each side by blunt dissection. Three implantation groups were studied: 1) DBM alone; 2) DBM with untreated PRP; and 3) DBM with PF4 depleted PRP. In each case, 50 milligrams (mg) of DBM were implanted in each site. The implants were subsequently inserted into the implantation muscle sites. Each animal received two implants from each group. The implantation sites with regard to placement in the rat were randomized. Explants were retrieved after 14- and 28-day implantation. One-half of each explant underwent histological staining and the second half was assayed for alkaline phosphatase activity by methods previously described.

Collagen sponge (Type I derived from bovine tendon) with size of 1 centimeter (cm)×1 cm was used as carrier for testing of PRP effect subcutaneously. Fisher 344 rats were used in this study. Collagen sponges were received following test group samples: 1) collagen alone; 2) collagen plus inactivated PRP; 3) collagen plus thrombin/Ca activated PRP; 4) collagen plus thrombin/no calcium PRP; 5) collagen plus PF4-depleted PRP (thrombin/Ca); and 6) collagen plus PF4-depleted PRP (thrombin/no calcium). Samples were implanted at the dorsal site of rats and each rat received four samples. Histology was applied to samples after 14- and 28-day implantation. Soft tissue ingrowth, inflammatory cells infiltration and capsulation were evaluated pathologically.

Depleted PF4 as an additive for bone formation on collagen/BMP was also studied in animals. Three test groups were implanted into abdominal muscles for bone cartilage and bone formation studied at 14 and 28 days. Three test groups as follows:

1) collagen sponge (1×1 cm2) loaded with 3.0 ug of rhBMP-2; 2) collagen sponge with 3.0 ug of BMP2 plus PRP; and 3) collagen sponge with 3.0 ug of BMP-2 plus PF4-depleted PRP.

Histological Evaluation

Explants were fixed in 10% neutral buffered formalin, decalcified on selected hard tissue in 5% formic acid, embedded in paraffin, sectioned, and stained with either hematoxylin and eosin (H&E) or Safranin-O. Three consecutive cross-sectional cuts were made at each of three different levels of the explant to visualize any induced cartilage and/or bone formation. Each section was evaluated for evidence of inflammation panel, fibrosis, soft tissue ingrowth, encapsulation, chondrogenesis and osteoinduction.

The repair response of musculoskeletal tissues generally starts with the formation of a blood clot and degranulation of platelets, which releases growth factors and cytokines at the site. This microenvironment results in chemotaxis of inflammatory cells as well as the activation and proliferation of local progenitor cells.

The present disclosure provides, among other things, PF4-depleted PRP that can be used for bone tissue repair in orthopedic, craniofacial and dental applications. PF4-depleted platelet releasate will stimulate migration and proliferation of osteogenic progenitor cells by increasing the proliferation of osteoblastic cells and matrix synthesis. PF4-depleted PRP will be applied by itself or combined with exogenous growth factors such as BMPs or other growth factors and cells.

The present disclosure provides, among other things, PF4-depleted PRP that can be applied in cartilage repair and regeneration, such as cartilage damage from osteoarthritis by injection or implantation. Alone or combined with scaffold, cells, and other growth factors, for repair or pain relief.

The present disclosure provides, among other things, PF4-depleted PRP that can be applied in degenerated intervertebral disc repair and regeneration alone or combined with scaffold, cells, and other growth factors.

For soft tissue repair, the growth factors associated with PRP will promote fibroblastic growth, differentiation and scar formation. The inventions of the present disclosure provide, among other things, PF4-depleted PRP that is a treatment for acute or chronic tendon and muscle disorders, such as helping to treat chronic Achilles tendonitis, patellar tendonitis and in rotator cuff repair, ACL repair, and meniscus repair in sports medicine.

The present disclosure provides, among other things, PF4-depleted PRP which enhances the proliferation of human adipose-derived stem cells for cell-based, soft-tissue and hard tissue engineering.

The present disclosure provides, among other things, PF4-depleted PRP, which enhances the proliferation of human dermal fibroblasts for wound healing, such as burn wound, diabetic ulcer, and chronic skin wound.

The present disclosure also provides other numerous benefits and advantages, some of which have been mentioned herein. The present disclosure provides, among other things, a biological active composite from platelet preparation for wound repair, improved and novel methods of repairing and regenerating hard or soft tissue, removing PF4 from platelet-containing blood preparation and reducing inflammation, anti-angiogenesis and anti-osteogenesis in the soft and hard tissue of a mammal.

It should be appreciated that the various embodiments of the present disclosure can be used alone or with one or more bone grafts, and for cartilage defect, tendon, ligament, skin, chronic wound, and para-operation sites.

The various embodiments can be used by themselves or with further composites, a collagen sponge, a collagen sheet, hydroxapatite granule, hydroxyapatite block, freeze-dried bone allograft (FDBA), demineralized bone matrix powder or putty, or sponge, TCP and other osteoconductive materials.

The embodiments of the present disclosure can also be mixed with the mammal's cells, including stem cells from bone marrow or fat tissue and/or allogenic stem cells from different sources of the mammal.

While the structures and methods have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

REFERENCES

The following references are incorporated herein by reference in their entirety.

1. Barrow, C. R. and G. C. Pomeroy (2005). "Enhancement of syndesmotic fusion rates in total ankle arthroplasty with the use of autologous platelet concentrate." *Foot Ankle Int* 26(6): 458-461.
2. Berghoff, W. J., W. S. Pietrzak, et al. (2006). "Platelet-rich plasma application during closure following total knee arthroplasty." *Orthopedics* 29(7): 590-8.
3. Bibbo, C., C. M. Bono, et al. (2005). "Union rates using autologous platelet concentrate alone and with bone graft in high-risk foot and ankle surgery patients." *J Surg Orthop Adv* 14(1): 17-22.
4. Everts, P. A., C. Brown Mahoney, et al. (2006). "Platelet-rich plasma preparation using three devices: implications for platelet activation and platelet growth factor release." *Growth Factors* 24(3): 165-71.
5. Everts, P. A., J. T. Knape, et al. (2006). "Platelet-rich plasma and platelet gel: a review." *J Extra Corpor Technol* 38(2): 174-87.
6. Frechette, J. P., I. Martineau, et al. (2005). "Platelet-rich plasmas: growth factor content and roles in wound healing." *J Dent Res* 84(5): 434-439.
7. Froum, S. J., S. S. Wallace, et al. (2002). "Effect of platelet-rich plasma on bone growth and osseointegration in human maxillary sinus grafts: three bilateral case reports." *Int J Periodontics Restorative Dent* 22(1): 45-53.
8. Maione, T. E., G. S. Gray, et al. (1990). "Inhibition of angiogenesis by recombinant human platelet factor-4 and related peptides." *Science* 247(4938): 77-9.
9. Nikolidakis, D., J. van den Dolder, et al. (2006). "The effect of platelet-rich plasma on the bone healing around calcium phosphate-coated and non-coated oral implants in trabecular bone." *Tissue Eng* 12(9): 2555-2563.
10. Ranly, D. M., C. H. Lohmann, et al. (2007). "Platelet-rich plasma inhibits demineralized bone matrix-induced bone formation in nude mice." *J Bone Joint Surg Am* 89(1): 139-147.
11. Scheuerer, B., M. Ernst, et al. (2000). "The CXC-chemokine platelet factor 4 promotes monocyte survival and induces monocyte differentiation into macrophages." *Blood* 95(4): 1158-66.
12. van den Dolder, J., R. Mooren, et al. (2006). "Platelet-rich plasma: quantification of growth factor levels and the effect on growth and differentiation of rat bone marrow cells." *Tissue Eng* 12(11): 3067-3073.
13. Weiner, B. K. and M. Walker (2003). "Efficacy of autologous growth factors in lumbar intertransverse fusions." *Spine* 28(17): 1968-1970.
14. Wolpe, S. D. and A. Cerami (1989). "Macrophage inflammatory proteins 1 and 2: members of a novel superfamily of cytokines." *FASEB J* 3(14): 2565-73.
15. Xia, C. Q. and K. J. Kao (2003). "Effect of CXC chemokine platelet factor 4 on differentiation and function of monocyte-derived dendritic cells." *Int Immunol* 15(8): 1007-15.
16. Zechner, W., S. Tangl, et al. (2003). "Influence of platelet-rich plasma on osseous healing of dental implants: a histologic and histomorphometric study in minipigs." *Int J Oral Maxillofac Implants* 18(1): 15-22.

The invention claimed is:

1. A method of repairing and regenerating a hard or soft tissue in a mammal, the method comprising:
    (a) preparing a platelet-rich plasma preparation comprising activated platelets, wherein the platelet-rich plasma preparation is further characterized as having the following properties:
        (i) it contains a reduced level of platelet factor 4 (PF4) relative to untreated controls,
        (ii) content and activity of growth factors in the platelet-rich plasma preparation are preserved, and
        (iii) it is free of other blood cells; and
    (b) administering to the mammal a therapeutic amount of the platelet-rich plasma preparation,
    wherein the therapeutic amount of the platelet-rich plasma preparation is effective to repair and regenerate the hard and soft tissue in the mammal.

2. The method of claim 1, wherein the platelet-rich plasma preparation is prepared from whole blood.

3. The method of claim 2, wherein the whole blood is autologous whole blood drawn from the mammal.

4. The method of claim 1, wherein the platelet-rich plasma preparation is administered to the mammal with at least one graft.

5. The method according to claim 4, wherein the graft is selected from the group consisting of: a bone graft, a skin graft, a cartilage graft, a ligament graft, a tendon graft, a peripheral nerve graft, and a combination thereof.

6. The method according to claim 4, further comprising administering at least one cell type selected from the group consisting of a tissue specific cell, a stem cell, an autologous cell, and an allogeneic cell prior to administering the platelet rich plasma preparation to the mammal.

7. The method according to claim 1, preparing step (a) further comprising:
    (1) activating platelets of the platelet-rich plasma preparation, thereby producing an activated platelet-rich plasma preparation;
    (2) adding to the activated platelet-rich plasma preparation a solid or semi-solid phase matrix conjugated with heparin, such that the solid or semi-solid phase matrix conjugated with heparin binds to at least some Platelet Factor 4 (PF4) in the activated platelet-rich plasma preparation; and
    (3) removing from the activated platelet-rich plasma preparation the solid or semi-solid phase matrix conjugated with heparin to which the Platelet factor 4 (PF4) is bound, thereby reducing the level of platelet factor 4 (PF4) relative to untreated controls.

8. The method of claim 7, wherein the solid or semi-solid phase heparin-conjugating matrix contains heparin-conjugated agarose beads, heparin-conjugated silica beads, heparin-conjugated Sepharose beads, heparin-Sephadex beads, heparin-conjugated alginate beads, heparin-conjugated, acrylic beads, or a combination thereof.

9. The method of claim 8, wherein the solid or semi-solid phase heparin-conjugating matrix is in the form of packed beads, column, a 3D mesh, hollow fibers, or a gel.

10. The method of claim 7, wherein binding of the solid or semi-solid phase matrix conjugated with heparin to at least some Platelet Factor 4 (PF4) in the platelet-rich plasma preparation is carried out by at least one method selected from the group consisting of: mass loading, batch loading, sequential loading, continuous loading, and a combination thereof.

11. The method of claim 7, wherein the platelet-rich plasma preparation is prepared from whole blood.

12. The method of claim 7, wherein the solid phase matrix conjugated with heparin is heparin-conjugated agarose.

13. The method of claim 7, wherein platelets of the platelet-rich plasma preparation are activated by adding a platelet-activation reagent to the platelet-rich plasma preparation.

14. The method of claim 13, wherein the platelet-activation reagent is selected from the group consisting of thrombin, collagen, thromboxane A2, ADP, and a combination thereof.

15. The method of claim 7, wherein platelets of the platelet-rich plasma preparation are activated spontaneously upon storage.

16. The method of claim 1, wherein the other blood cells are red blood cells.

17. A method of reducing inflammation, anti-angiogenesis and anti-osteogenesis in a soft and hard tissue of a mammal, the method comprising:
  administering to the mammal a therapeutic amount of a platelet-rich plasma preparation comprising activated platelets,
  wherein the platelet-rich plasma preparation is further characterized as having the following properties:
  (i) it contains a reduced level of Platelet Factor 4 (PF4) relative to untreated controls,
  (ii) content and activity of growth factors in the platelet-rich plasma preparation are preserved, and
  (iii) it is free of other blood cells; and
  wherein the therapeutic amount of the platelet-rich plasma preparation is effective to reduce inflammation, anti-angiogenesis and anti-osteogenesis in the mammal.

18. The method of claim 17, wherein the platelet-rich plasma preparation is prepared from whole blood.

19. The method of claim 17, wherein the Platelet Factor 4 (PF4)-reduced platelet rich plasma preparation is administered to the mammal with at least one graft.

20. The method according to claim 19, wherein the graft is selected from the group consisting of: a bone graft, a skin graft, a cartilage graft, a ligament graft, a tendon graft, a peripheral nerve graft, and a combination thereof.

21. The method according to claim 19, further comprising administering at least one cell type selected from the group consisting of a tissue specific cell, a stem cell, an autologous cell, and an allogeneic cell prior to administering the platelet rich plasma preparation to the mammal.

22. The method of claim 18, wherein the whole blood is autologous whole blood drawn from the mammal.

23. The method of claim 17, wherein the platelet-rich plasma preparation is administered to a wound site of the mammal.

24. The method of claim 23, wherein the platelet rich plasma preparation is administered together with a wound dressing.

* * * * *